United States Patent
Hill et al.

(10) Patent No.: US 9,326,851 B2
(45) Date of Patent: May 3, 2016

(54) AUTOMATIC SUTURE FIXATION APPARATUS FOR MINIMALLY INVASIVE SURGERY

(76) Inventors: J. Donald Hill, Tiburon, CA (US); Geoff Briggs, Los Altos, CA (US); Michael Sims, Montara, CA (US); Cameron Dale Hinman, Woodside, CA (US)

(*) Notice: Subject to any disclaimer, the term of this patent is extended or adjusted under 35 U.S.C. 154(b) by 2009 days.

(21) Appl. No.: 11/674,372

(22) Filed: Feb. 13, 2007

(65) Prior Publication Data

US 2007/0135911 A1    Jun. 14, 2007

Related U.S. Application Data

(63) Continuation of application No. 09/987,976, filed on Nov. 16, 2001, now Pat. No. 7,175,659.

(60) Provisional application No. 60/248,837, filed on Nov. 16, 2000.

(51) Int. Cl.
*A61F 2/24* (2006.01)
*A61B 17/04* (2006.01)

(52) U.S. Cl.
CPC ........... *A61F 2/2427* (2013.01); *A61B 17/0469* (2013.01); *A61B 17/0482* (2013.01); *A61B 2017/0496* (2013.01)

(58) Field of Classification Search
CPC ........ A61F 2/24; A61F 2/2427; A61F 2/2409
USPC ............... 623/2.14, 2.11, 2.37, 2.4, 2.2–2.35, 623/2.38–2.41; 606/148, 228, 151, 232; 128/898
See application file for complete search history.

(56) References Cited

U.S. PATENT DOCUMENTS

| | | | |
|---|---|---|---|
| 3,409,013 A * | 11/1968 | Berry | 606/1 |
| 4,182,446 A | 1/1980 | Penny | |
| 4,211,325 A * | 7/1980 | Wright | 206/438 |
| 4,612,011 A | 9/1986 | Kautzky | |
| 4,702,250 A | 10/1987 | Ovil et al. | |
| 4,986,023 A | 1/1991 | Bucholz | |
| 5,601,576 A | 2/1997 | Garrison | |
| 5,716,370 A | 2/1998 | Williamson, IV et al. | |
| 5,766,240 A * | 6/1998 | Johnson | 623/2.39 |
| 5,776,188 A | 7/1998 | Shepherd et al. | |
| 5,800,531 A | 9/1998 | Cosgrove et al. | |
| 5,908,378 A | 6/1999 | Kovacs et al. | |
| 6,066,160 A | 5/2000 | Colvin et al. | |
| 6,113,632 A | 9/2000 | Reif | |
| 6,176,877 B1 | 1/2001 | Buchanan et al. | |
| 6,203,553 B1 * | 3/2001 | Robertson et al. | 606/139 |
| 6,716,243 B1 | 4/2004 | Colvin et al. | |
| 6,790,229 B1 * | 9/2004 | Berreklouw | 623/2.1 |
| 2002/0082686 A1 | 6/2002 | Nguyen-Thien-Nhon et al. | |

* cited by examiner

*Primary Examiner* — Brian Pellegrino
(74) *Attorney, Agent, or Firm* — Baker Botts L.L.P.

(57) ABSTRACT

An apparatus for automatically fixing sutures used in the surgical replacement of a heart valve, including a first cylinder having a first end and a second end and an interior surface and an exterior surface, and first means for securing fixing suture formed on the exterior surface adjacent to the second end of the first cylinder. The apparatus also includes a second cylinder having second means for securing fixing suture formed on an interior surface of the second cylinder, such that the second means corresponds to and fixedly engages the first means for securing fixing suture, and the first means and the second means secure fixing sutures therebetween.

16 Claims, 11 Drawing Sheets

AUTOMATIC SUTURE FIXATION APPARATUS FOR MINIMALLY INVASIVE SURGERY

This application is a divisional application of and claims priority from U.S. patent application Ser. No. 09/987,976, which was filed on Nov. 16, 2001, which claims priority from U.S. Provisional Patent Application No. 60/248,837, which was filed on Nov. 16, 2000, the disclosures of which are incorporated by reference in their entirety.

BACKGROUND OF THE INVENTION

1. Field of the Invention

The invention relates to apparatus for automatic suture fixation and methods for minimally invasive cardiac surgery employing such apparatus. In particular, the invention relates to apparatus for automatic suture fixation including a first cylinder fitted with first securing means on its exterior surface and a second cylinder with second securing means on its interior surface, whereby sutures may be secured between these cylinders when the corresponding securing means engage. Further, methods for minimally invasive cardiac surgery employing such apparatus may include the steps of threading the sutures used to secure a replacement heart valve over the exterior surface of the first cylinder and over the interior surface of the second cylinder, applying pressure against the first cylinder to secure it against the replacement valve, and applying tension against the sutures to achieve a blood-tight seal between the replacement valve and the heart, before securing the sutures between the first and second cylinders.

2. Description of Related Art

Current methods of placing replacement heart valves, including prosthetic valves, harvested pig valves, and human donor valves, require the careful placement and tying-off of numerous sutures. In heart valve replacement surgery, a damaged, defective, or diseased heart valve is removed to provide an annulus for securing a replacement valve. In order to prepare the annulus to receive the replacement valve, traction stitches may be placed through the annulus from both the superior and inferior aspects of the annulus. By applying tension to these sutures, the annulus may be better exposed to facilitate positioning of the replacement valve.

Replacement valves may be fitted with a sewing ring, which surrounds the valve and allows it to be more tightly secured to the annulus without penetrating the valve structure. A surgeon may use interrupted mattress stitching to secure the replacement valve to the annulus. Mattress stitches are chosen to allow more exact tissue to replacement valve edge approximation.

The individual sutures may be made from a 2/0 synthetic material and are fitted with curved needles at each end. The natural curve of these needles aids the surgeon in guiding the needle tips away from coronary arteries including the coronary sinus and in avoiding inadvertent penetration of the fat of the atrioventricular groove. In addition, the sutures are preferably selected, such that alternating colors of suture may be used to secure the replacement valve to the annulus. By using alternating colors of suture, the surgeon may more readily keep track of the sutures, as he or she ties them off to secure the replacement valve to the annulus. Alternating suture colors reduces the risk that the ends of discontinuous sutures will be tied together, resulting in an improperly secured replacement value and the possibility of leakage or failure of the replacement valve.

A holder may be used to position the replacement away from the annulus while the annulus is prepared to receive the replacement valve. The surgeon applies the sutures, e.g., about 18 to 24 sutures on average, such that the sutures pass through the sewing ring of the replacement valve and then through the annulus, posteriorly. Pledgets, such as compressed Teflon® felt pledgets, may be threaded separately onto the suture to strengthen the attachment of the replacement valve to the annulus. The initial pass from the posterior face of the annulus may be completed in a counterclockwise direction around the annulus. The surgeon then may pass sutures through the anterior face of the annulus and pass the suture through the sewing ring of the replacement valve. This anterior stitching may be completed in a clockwise direction. By shifting the position of the replacement valve (or the replacement valve holder) with respect to the annulus and by applying tension to the traction stitches, the surgeon may expose the annulus in the manner that facilitates the placement of securing sutures.

Once the surgeon has completed the placement of the sutures, the surgeon may place tension on the sutures and slide the replacement valve into position within the annulus. The surgeon then ties off the sutures in the order in which they were placed—first the posteriorly placed sutures followed by the anteriorly placed sutures. As each suture is tied off, the surgeon reconfirms that the replacement valve remains properly positioned and securely sealed to the annulus, so that he or she may attain a blood-tight seal between the replacement valve and the annulus.

Because of the necessity for the careful placement of the replacement valve within the annulus and the requirement that each pair of suture ends are individually tied, heart valve replacement surgery may be lengthy, requiring the patient to spend an extended period of time under anesthesia. Further, because the patient's heart must be stopped during heart valve replacement surgery, a lengthy surgery requires the patient to spend an extended period with breathing and circulation supported by a heart-lung (or heart by-pass) machine. An extended period under anesthesia and on a heart-lung machine may complicate and delay the recovery process.

In addition, as noted above, the surgeon confirms that the replacement valve remains properly positioned within the annulus after each pair of suture ends is tied, and the surgeon ensures that only continuous suture ends are tied together. Thus, the surgeon needs sufficient room to observe the suture attachment and the positioning of the replacement valve and to manipulate the sutures in close proximity to the patient's heart. This may be extremely difficult to achieve in minimally-invasive cardiac surgery (MICS), in which the surgeon may be required to operate through an opening in the patient's chest with a small diameter, e.g., between about 2 cm and about 3 cm. Further, the patient's heart may be positioned between about 10 cm and about 12 cm below the chest opening. Larger openings generally increases the risk associated with the surgery and increase the patient's recovery time. Therefore, in order to accomplish valve replacements using MICS techniques, surgeons frequently resort to a knot tying device to push the suture knots down into the patient's chest opening.

SUMMARY OF THE INVENTION

Thus, a need has arisen for apparatus and methods, which permit surgeons to secure sutures within the limitations imposed by MICS. In particular, a need has arisen for apparatus and methods, which permit surgeons to quickly and accurately secure sutures.

It is a feature of the present invention that it permits surgeons to operate within the extremely confined spaces available in MICS or in the more larger spaces available in more traditional open, heart surgery. It is an additional feature that the present invention reduces or eliminates suture tying errors by reducing or eliminating the need for tying individual suture pairs. It is yet another feature of the present invention that sutures may be trimmed flush with the valve replacement apparatus, thus reducing or eliminating the suture ends as a potential source of irritation and eliminating the knots as a possible cause of leakage or valve replacement failure.

It is an advantage of the present invention that it permits surgical time to be reduced, thereby reducing the amount of time that a patient remains under anesthesia and on a heart-lung machine. By reducing each of these aspects of the surgical procedure, the patient's prospects for recovery may be improved, and the patient's recovery may be accelerated. It is a further advantage of the present invention that by reducing the time required to secure the heart valve replacement, the amount of time required to complete heart valve replacement surgery may be reduced. This may result in decreased surgical costs due to more efficient use of surgical resources, e.g., operating rooms and monitors and anesthesia equipment; more efficient use of surgeon's time; and shortened hospital stays after heart valve replacement surgery.

In an embodiment, the invention is an apparatus for automatically fixing sutures used in the surgical replacement of a heart valve. The apparatus comprises a first cylinder having a first end and a second end and an interior surface and an exterior surface and a valve sleeve including an annular cuff surrounding the exterior surface adjacent to the first end of the first cylinder. First securing means are formed on the exterior surface adjacent to the second end of the first cylinder, and a replacement heart valve is positioned within the valve sleeve. The apparatus further comprises a second cylinder having second securing means formed on an interior surface of the second cylinder, such that the second securing means correspond to and are adapted to fixedly engage the first securing means.

In another embodiment, the invention again is an apparatus for automatically fixing sutures used in the surgical replacement of a heart valve. The apparatus comprises a first cylinder having a first end and a second end and an interior surface and an exterior surface, and a valve sleeve including an annular cuff and a plurality of securing struts surrounding the exterior surface adjacent to the first end of the first cylinder. These struts extending beyond the first end of the first cylinder. First securing means are formed on the exterior surface adjacent to the second end of the first cylinder, and a replacement heart valve is positioned within the valve sleeve. the replacement heart valve has a circumferential outer edge, wherein the circumferential outer edge is affixed to the valve sleeve. The apparatus further comprises a second cylinder having second securing means formed on an interior surface of the second cylinder, such that the second securing means corresponds to and is adapted to fixedly engage the first securing means.

In still another embodiment, the invention also is an apparatus for automatically fixing sutures used in the surgical replacement of a heart valve. The apparatus comprises a first cylinder having a first end and a second end and an interior surface and an exterior surface, a valve sleeve including an annular cuff, and a prosthetic heart valve positioned within the first cylinder and affixed to the valve sleeve. The valve sleeve surrounds the exterior surface adjacent to the first end of the first cylinder, and first securing means are formed on the exterior surface adjacent to the second end of the first cylinder. The apparatus further comprises a second cylinder having second securing means formed on an interior surface of the second cylinder, such that the second securing means corresponds to and are adapted to fixedly engage the first securing means.

In yet another embodiment, the invention is a method for automatically fixing sutures to secure a valve sleeve including an annular cuff and a replacement heart valve, to an annulus formed in a patient's heart. The method comprises the steps of removing an existing heart valve, thereby forming an annulus in the patient's heart and placing a first cylinder having a first end and a second end and an interior surface and an exterior surface within the annulus. The first cylinder comprises first securing means formed on the exterior surface adjacent to the second end of the first cylinder. The first cylinder includes a valve sleeve having an annular cuff, such that the annular cuff surrounds the exterior surface adjacent to the first end of the first cylinder. The annular cuff of the valve sleeve then is positioned in the annulus and securing the cuff to the annulus with a plurality of sutures, and the plurality of sutures are threaded over the exterior surface of the first cylinder and over an interior surface of a second cylinder. The second cylinder has second securing means corresponding to and adapted to fixedly engage the first securing means of the first cylinder. Pressure then is applied against the first cylinder, and tension is applied to the plurality of sutures to ensure a blood-tight seal between the cuff of the valve sleeve and the annulus. The plurality of sutures then may be secured between the first cylinder and the second cylinder by engaging the first securing means of the first cylinder with the second securing means of the second cylinder.

In yet a further embodiment, the invention again is a method for automatically fixing sutures to secure a valve sleeve including an annular cuff and a replacement heart valve to an annulus formed in a patient's heart. The method comprises the steps of removing an existing heart valve thereby forming an annulus in the patient's heart, positioning the annular cuff of the valve sleeve in the annulus, and securing the cuff to the annulus with a plurality of sutures. The method further comprises the steps of placing a first cylinder having a first end and a second end and an interior surface and an exterior surface within the valve sleeve, such that the annular cuff surrounds the exterior surface adjacent to the first end of the first cylinder. The first cylinder also comprises first securing means formed on the exterior surface adjacent to the second end of the first cylinder. The plurality of sutures then are threaded over the exterior surface of the first cylinder and over an interior surface of a second cylinder. The second cylinder has second securing means corresponding to and adapted to fixedly engage the first securing means of the first cylinder. Pressure is then applied against the first cylinder, and tension is applied to the plurality of sutures to ensure a blood-tight seal between the cuff of the valve sleeve and the annulus. The plurality of sutures then are secured between the first cylinder and the second cylinder by engaging the first securing means of the first cylinder with the second securing means of the second cylinder.

Other objects, features and advantages of the invention will be apparent to those skilled in the art from the following detailed description of preferred embodiments and the accompanying drawings.

BRIEF DESCRIPTION OF THE DRAWINGS

The invention may be better understood with reference to the following drawings of preferred embodiments of the invention, in which:

FIGS. 2-1 and 2-2 depict cross-sectional views of the first and second cylinders, including embodiments of the corresponding, first and second securing means;

FIGS. 3-1 and 3-2 depict a plan view of the first cylinder of FIG. 2-2 and an enlarged view of a portion of this first cylinder showing circumferentially arranged suture-relief holes;

DETAILED DESCRIPTION OF PREFERRED EMBODIMENTS

Figure 1:
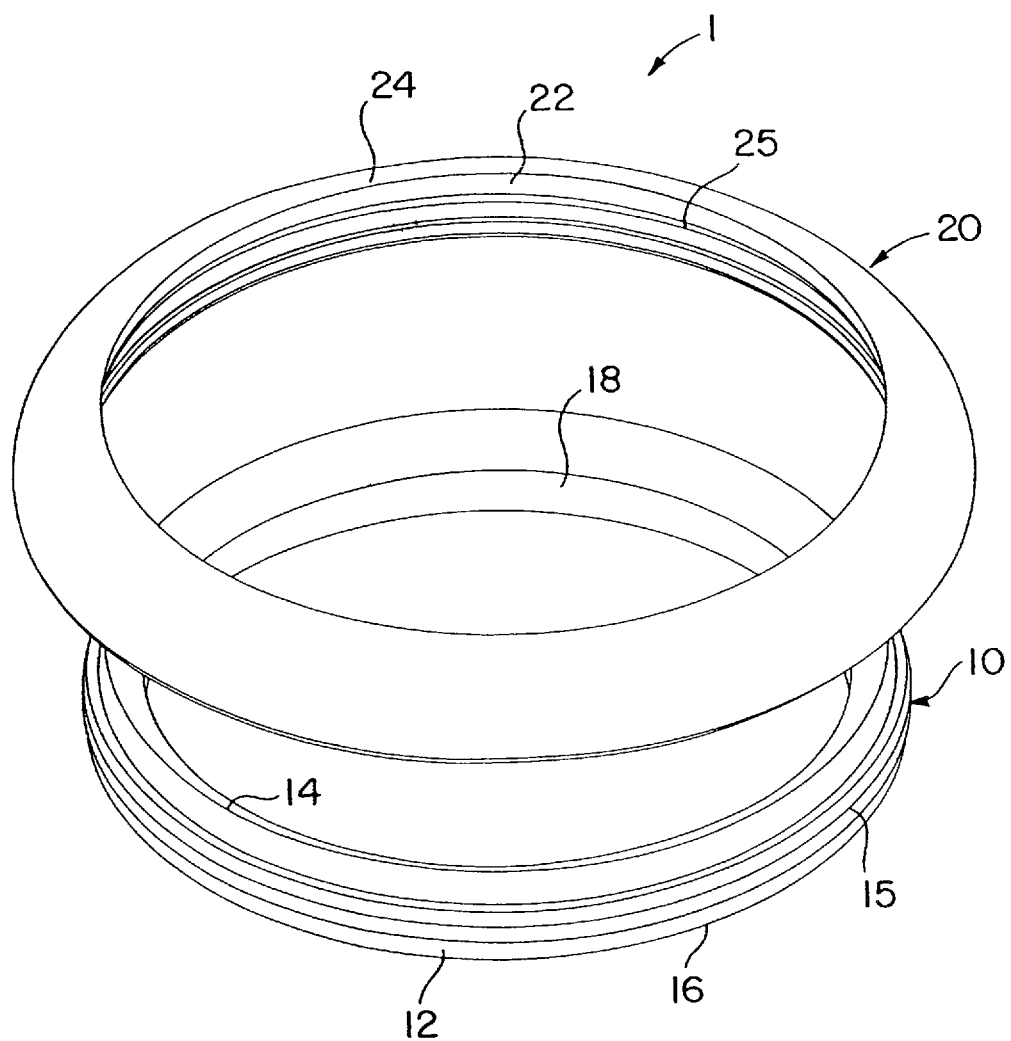
FIG. 1 depicts an embodiment of the apparatus including a first cylinder and a second cylinder.

Referring to FIG. 1, an embodiment of the apparatus 1 is depicted including a first cylinder 10 and a second cylinder 20. The material for cylinders 10 and 20 is chosen to be bio-compatible and anti-thrombogenic. Cylinders 10 and 20 may be made from a suitable metal or plastic, such as Delrin® plastic, manufactured by E.I. DuPont de Nemours and Co. of Wilmington, Del., pyrolitic carbon, or a Titanium-Nickel (95%-5%) alloy. Cylinders 10 and 20 must sufficiently rigid to hold the replacement valve securely during its surgical insertion, but sufficiently flexible to allow second cylinder 20 to be snapped into place over first cylinder 10. Preferably, first cylinder 10 is slightly more rigid than second cylinder 20, so that second cylinder 20 may be snapped into place over first cylinder 10.

First cylinder 10 comprises an exterior surface 12 and an interior surface 18 and a second (or upper) end 14 and a first (or lower) end 16. Further, first cylinder 10 includes a first securing means 15. Similarly, second cylinder 20 comprises an interior surface 22 and a first (or upper) end 24. Second cylinder 20 also includes a second securing means 25. Second securing means 25 correspond to and are adapted to engage first securing means 15. For example, first securing means 15 may be an annular lip and second securing means 25 may be a corresponding annular groove, or vice versa.

Figure 2:
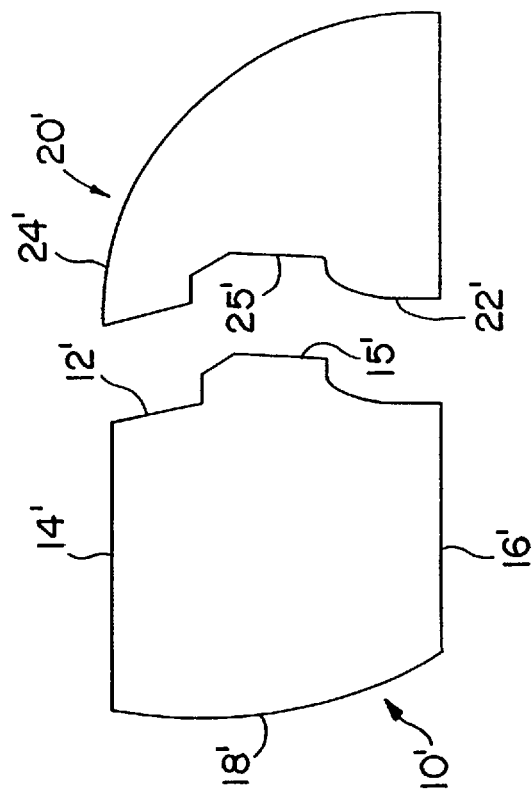
Figures 1, 2:
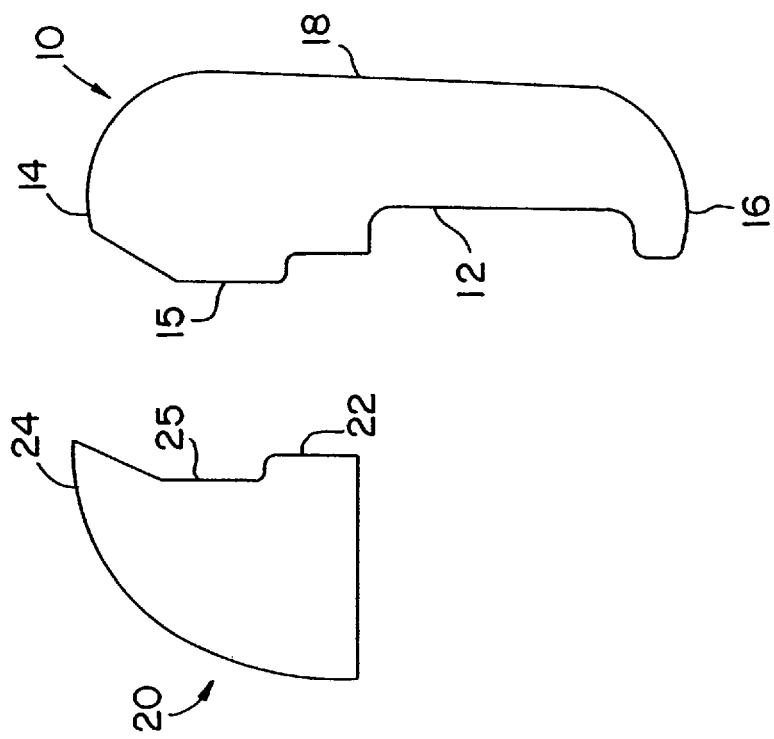

Referring to FIGS. 2-1 and 2-2, cross-sectional views of versions of first cylinder 10 and second cylinder 20, including embodiments of the corresponding securing means 15 and 25, respectively. In particular, the version depicted in FIG. 2-1 is configured to receive a valve sleeve (not shown) with an annular cuff (not shown) around the lower portion of first cylinder 10. Consequently, first cylinder 10 may have a height of about 5.25 mm, and second cylinder 20 may have a height of about 2.49 mm.

The valve sleeve may be manufactured from a surgical fabric, such as a surgical fabric selected from the group consisting of a Dacron® fabric, a Teflon® fabric, a Gore-Tex® fabric, and the like. In this version, a replacement valve (not shown), such as a heart valve harvested from a human donor or a heart valve harvested from a pig, is attached to the valve sleeve. For example, the replacement heart valve may include a sewing ring by which the valve may be sutured to the valve sleeve.

In the version depicted in FIG. 2-2, first cylinder 10' again is configured to engage second cylinder 20'. Specifically, first securing means 15' engage second securing means 25'. By comparison with FIG. 2-1, it is evident that first cylinder 10' is shorter than first cylinder 10, and that first cylinder 10' lacks the portion configured to receive a valve sleeve (not shown) with an annular cuff (not shown) around the lower portion of first cylinder 10'. Although first cylinder 10' also is configured to receive a valve sleeve (not shown) with an annular cuff (not shown), first cylinder 10' is designed to receive a prosthetic heart valve (not shown) within its circumference. Such a prosthetic heart valve may be attached directly to the valve sleeve without the addition of a sewing ring. Consequently, the heights of first cylinder 10' and second cylinder 20' are substantially the same and substantially equal to about 3.25 mm.

Figures 1, 3:
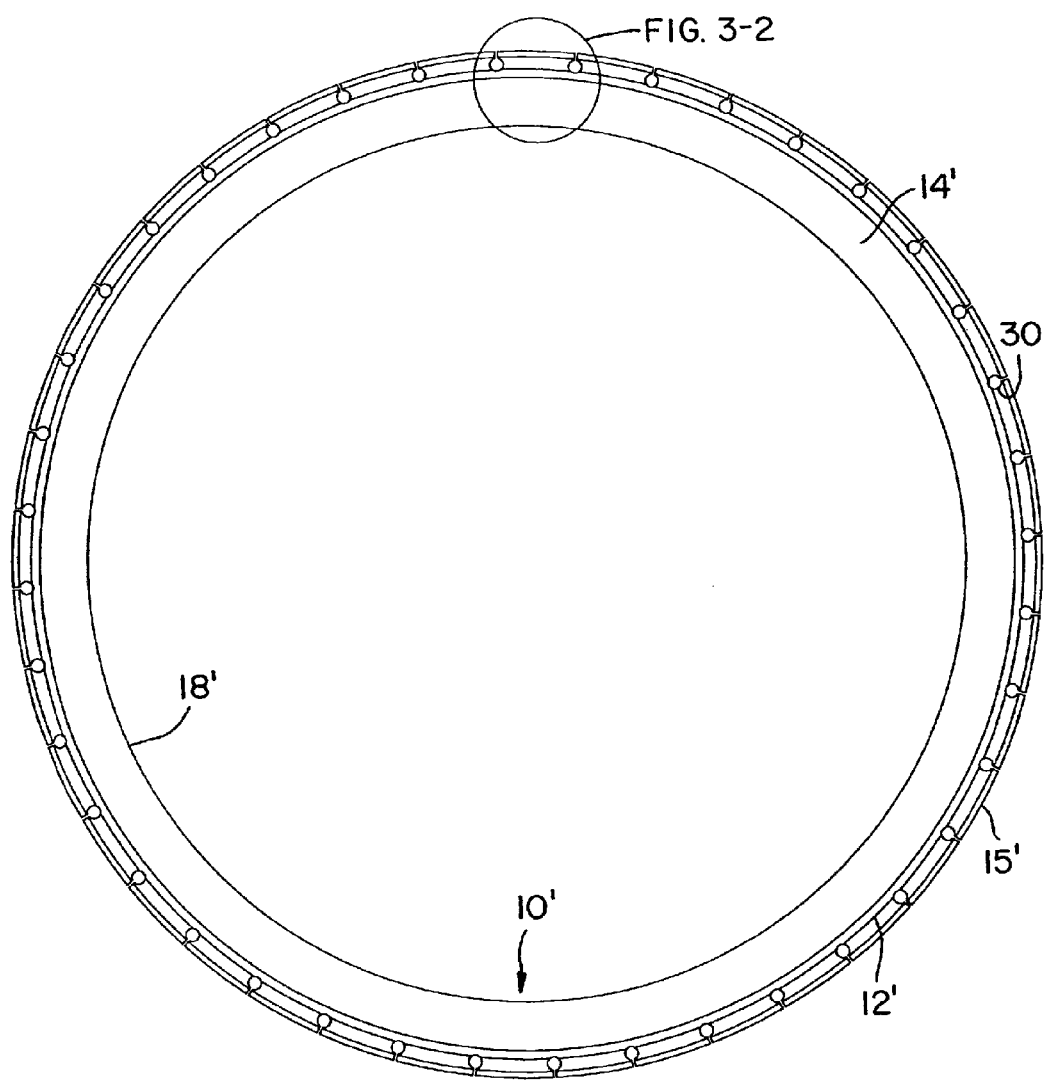
Figures 2, 3:
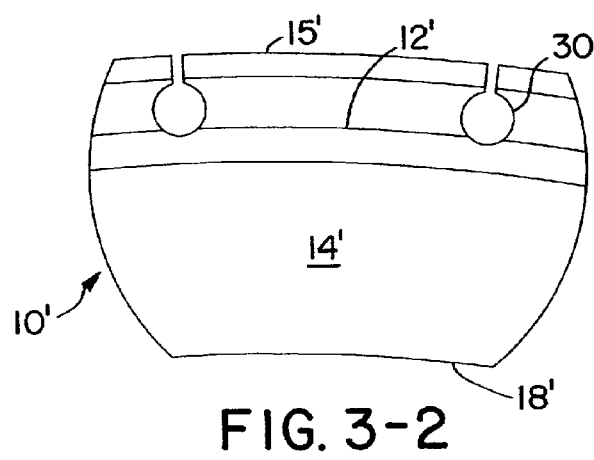

Referring to FIG. 3-1, a plan view of another version of first cylinder 10' of FIG. 2-2 is shown. In this version, cylinder 10' has been adapted to receive at least one of a plurality of securing sutures (not shown) into each of a plurality of relief holes 30, e.g., 40 relief holes spaced at 9° intervals, arrayed around the exterior surface of first cylinder 10'. In particular, relief holes 30 may be formed within first securing means 15', so that the sutures may be tightly secured between first cylinder 10' and second cylinder 20' when first securing means 15' engages second securing means 25'. As discussed below, suture may be passed through the annular cuff (not shown) and through the annulus formed by the removal of a damaged, defective, or diseased valve from the patient's heart. An enlarged view of a portion of first cylinder 10' showing circumferentially arranged, suture-relief holes 30 is shown in FIG. 3-2.

Figure 4:
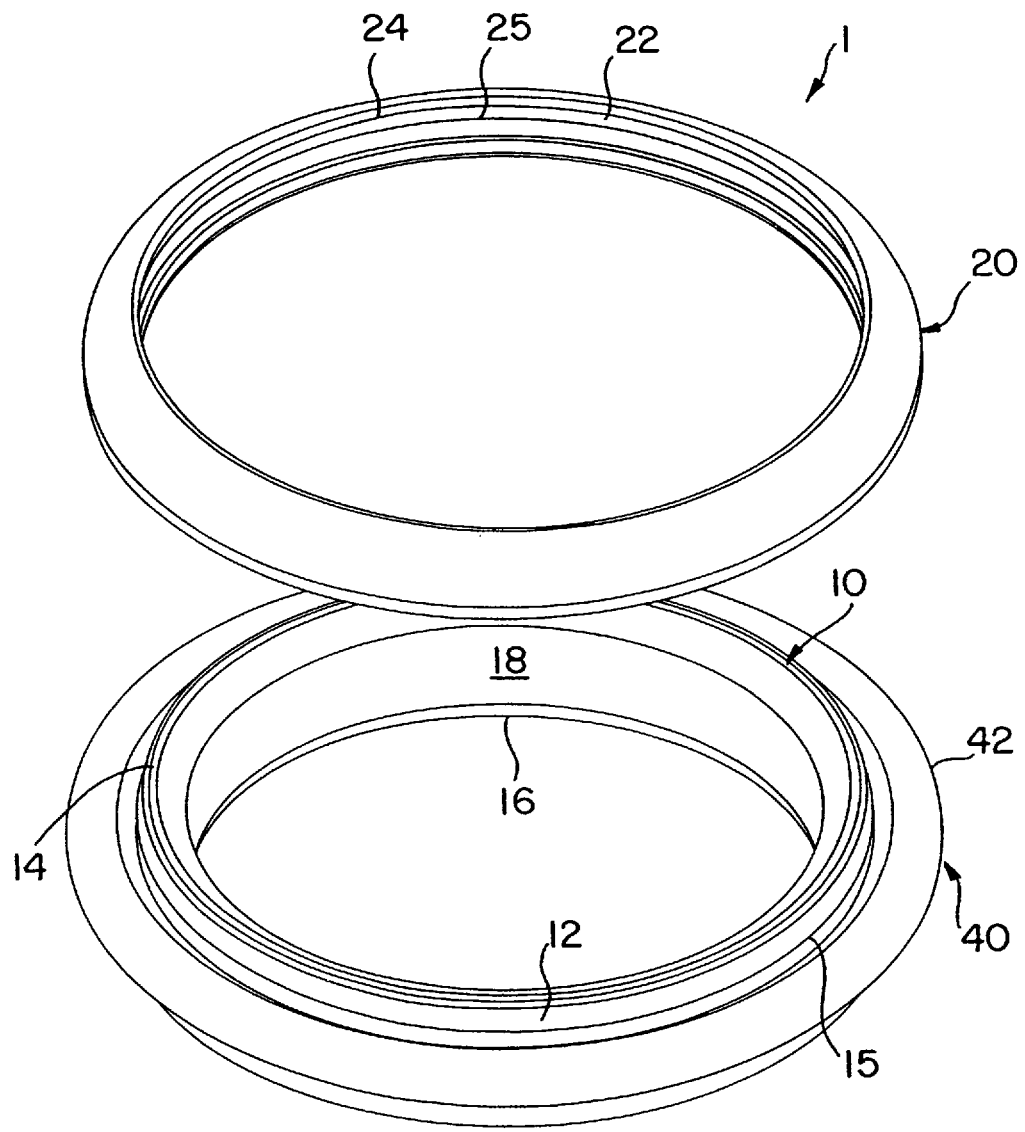
FIG. 4 depicts another embodiment of the apparatus including a first cylinder and a second cylinder, with a valve sleeve surrounding the lower portion of the exterior surface of the first cylinder.

In FIG. 4, another embodiment of the apparatus is depicted including first cylinder 10 and second cylinder 20. In this embodiment, a valve sleeve 40 surrounds the lower portion of exterior surface 12 of the first cylinder 10. Valve sleeve 40 includes an annular cuff 42 for securing apparatus 1 to an annulus formed in the patient's heart. As noted above, valve sleeve 40 may be manufactured from a surgical fabric, such as a surgical fabric is selected from the group consisting of a Dacron® fabric, a Teflon® fabric, a Gore-Tex® fabric, and the like.

Figure 5:
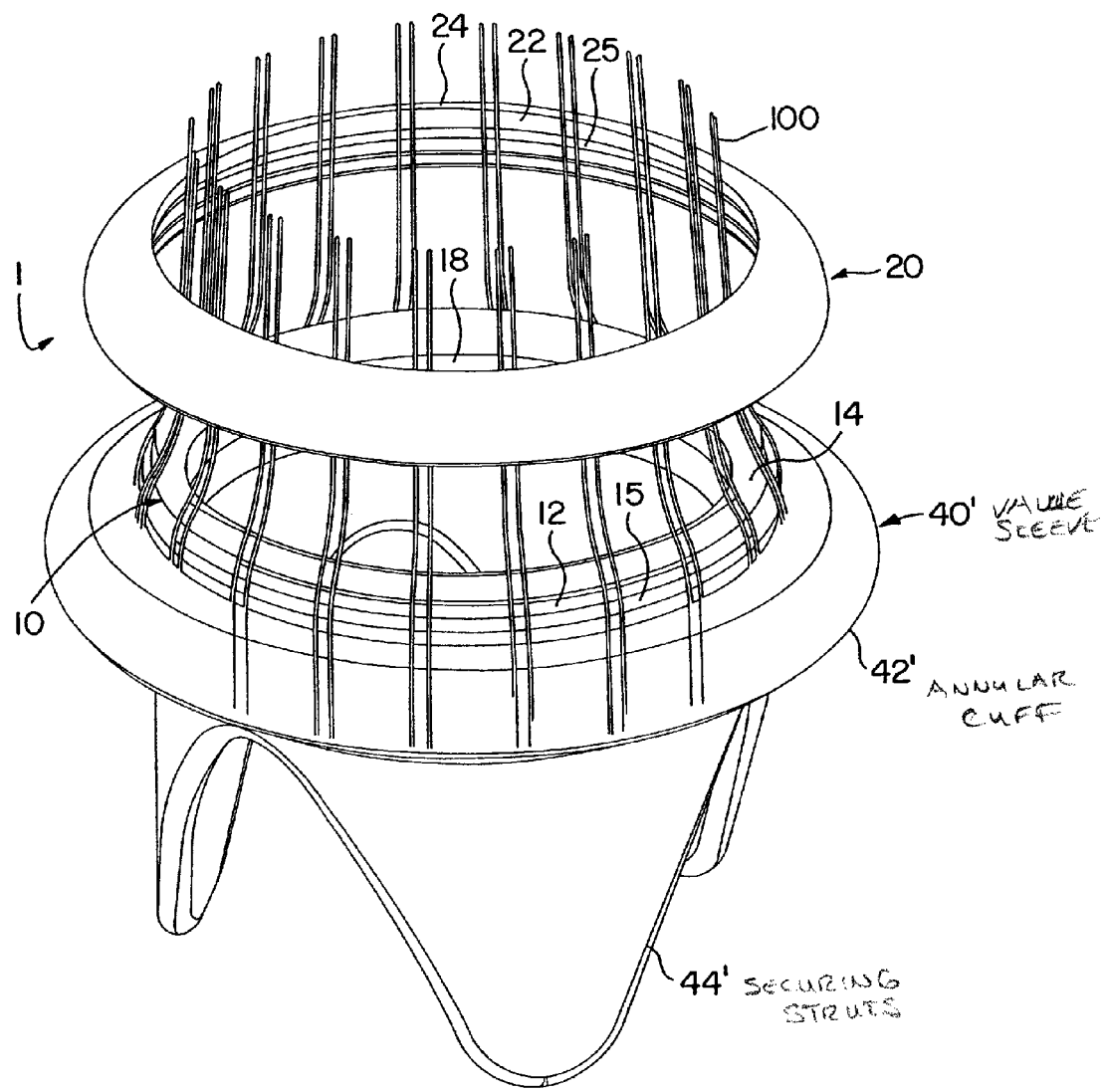
FIG. 5 depicts yet another embodiment of the apparatus including a first cylinder and a second cylinder, with a valve sleeve having an annular cuff and three securing struts.

Referring to FIG. 5, yet another embodiment of apparatus 1 includes first cylinder 10, second cylinder 20, and valve sleeve 40' having annular cuff 42' and three securing struts 44'. Valve sleeve 40' is manufactured from a surgical fabric, such as a surgical fabric is selected from the group consisting of a Dacron® fabric, a Teflon® fabric, a Gore-Tex® fabric, and the like. In this version, a replacement valve (not shown), such as a heart valve harvested from a human donor or a heart valve harvested from a pig, is attached to valve sleeve 40' at securing struts 44'. For example, the replacement heart valve may include a sewing ring by which the valve may be sutured to securing struts 44'.

As shown in FIG. 5 and discussed above, apparatus 1 is secured to the annulus formed in the patient's heart by means of sutures passed through annular cuff 42' and the annulus. Suitable suture may be made from a 2/0 synthetic material and are fitted with curved needles at each end. In addition, as with known methods of securing replacement valves to an annulus formed in a patient's heart, pledgets, such as compressed Teflon® felt pledgets, may be threaded separately onto the suture to strengthen the attachment of the replacement valve to the annulus. However, because of the importance of attaining and maintaining a blood-tight seal between apparatus 1 and the annulus, and in view of the rigid structure of first cylinder 10 and second cylinder 20, the pledgets must not be placed between apparatus 1 and the annulus.

Figure 6:
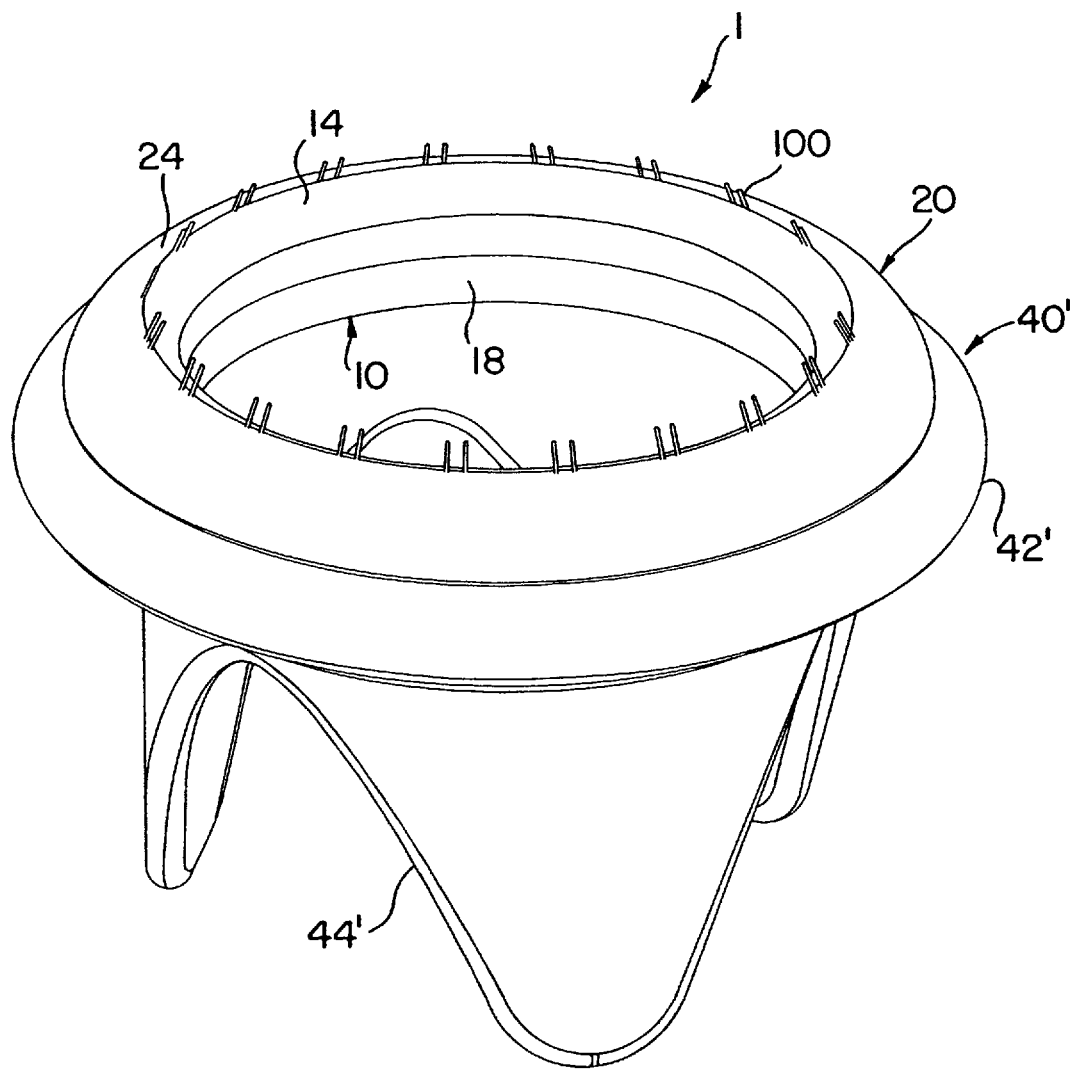
FIG. 6 depicts the embodiment of FIG. 5, wherein the securing means of the first and second cylinders are snapped into engagement, and the secured sutures have been trimmed.

Once annular cuff 42' is sutured to the annulus the end pairs of each suture 100 are passed over exterior surface 12 and first securing means 15 of first cylinder 10 and over interior surface 22 and second securing means 25. By applying tension to the sutures 100 and pressure to second end 14 of first cylinder 10, annular cuff 42' may be tightly sealed against the annulus. Once this seal is established, second cylinder 20 may be pressed down onto first cylinder 10, so that first sealing means 15 may engage second sealing means 25 and thereby seize sutures 100 within apparatus 1. Referring to FIG. 6, the embodiment of FIG. 5 is depicted, wherein the securing means of first and second cylinders 10 and 20 are snapped into engagement, and the secured sutures have been trimmed.

Figure 7:
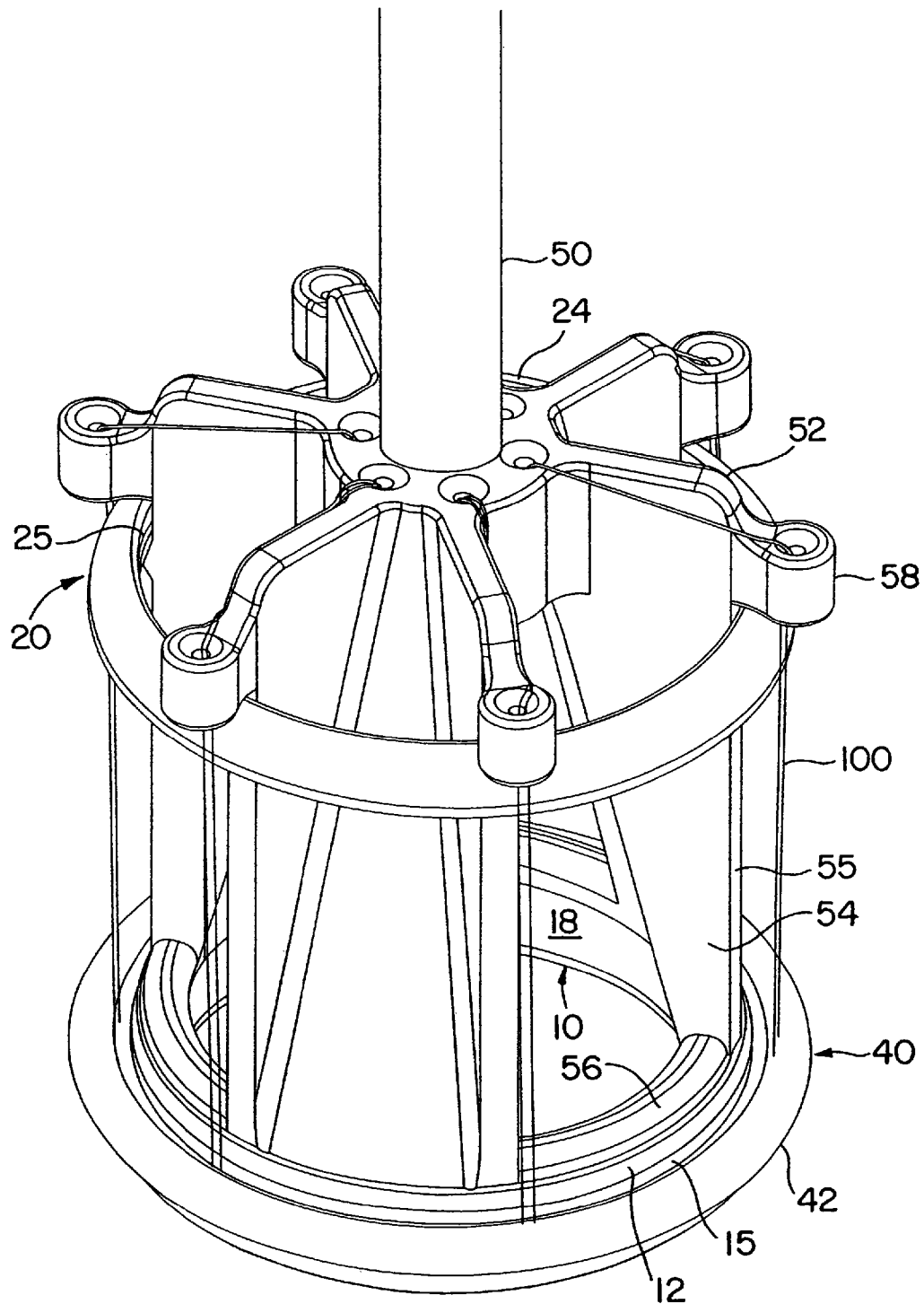
FIG. 7 depicts the embodiment of FIG. 4 mounted on a guiding rod.

In FIG. 7, the embodiment of apparatus I of FIG. 4 is depicted mounted on a guiding rod 50. Guiding rod 50 includes a rod end piece 52 formed at a first end of guiding rod 50. Rod end piece 52 has six support brackets 54 extending from rod end piece 52. and a guiding ring 56 affixed to support brackets 54. Ring 56 is adapted to engage second end 14 of first cylinder 10. Moreover, interior surface 22 of second cylinder 20 slidingly engages an exterior surface 55 of each of support brackets 54.

Again referring to FIG. 7, at least one eyelet 58 is formed on each of supporting brackets 54 for receiving at least one suture 100. By threading sutures 100 through eyelets 58, guiding ring 56 may be guided into contact with second end 14 of first cylinder 10. Tension applied to sutures 100 and pressure applied against guiding ring 56 to seal first cylinder 10 and its attached annular cuff 42 against the annulus.

Figure 8:
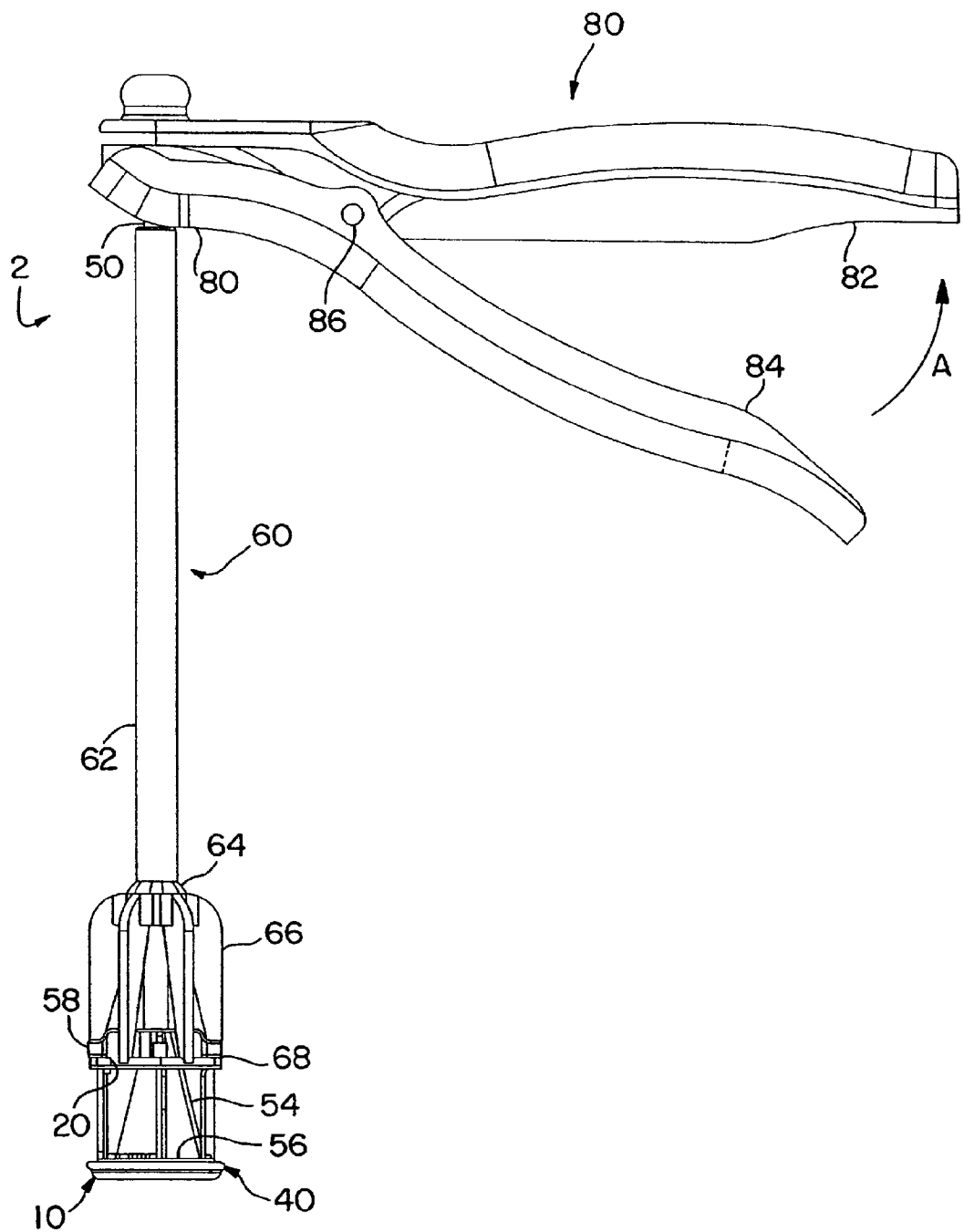
FIG. 8 depicts the embodiment of FIG. 4 mounted on an insertion device including a guiding rod, securing member, and urging means.

Referring to FIG. 8, the embodiment of FIG. 4 is depicted mounted on an insertion device 2 including guiding rod 50, a securing member 60, and urging means 80. Securing member 60 includes a rod sleeve 62, which slidingly engages guiding rod 50. A sleeve end piece 64 is formed on a first end of rod sleeve 62. Sleeve end piece 64 has six securing brackets 66, which are adapted to engage second cylinder 20 and which are angularly offset and positioned to interfit with support brackets 54. Insertion device 2 further comprises urging means 80 for sliding securing member 60 on guiding rod 50, whereby second securing means 25 of second cylinder 20 is urged into engagement with first securing means 15 on first cylinder 10. Urging means 80 comprise a handle 82 fixed substantially perpendicular to guiding rod 50 and a grip 84 pivotally attached by a pin 86 to handle 82. When grip 84 is pivoted on pin 86 in the direction of Arrow A, a levered projection 88 urges securing member 60 towards rod end piece 52.

Figure 9:
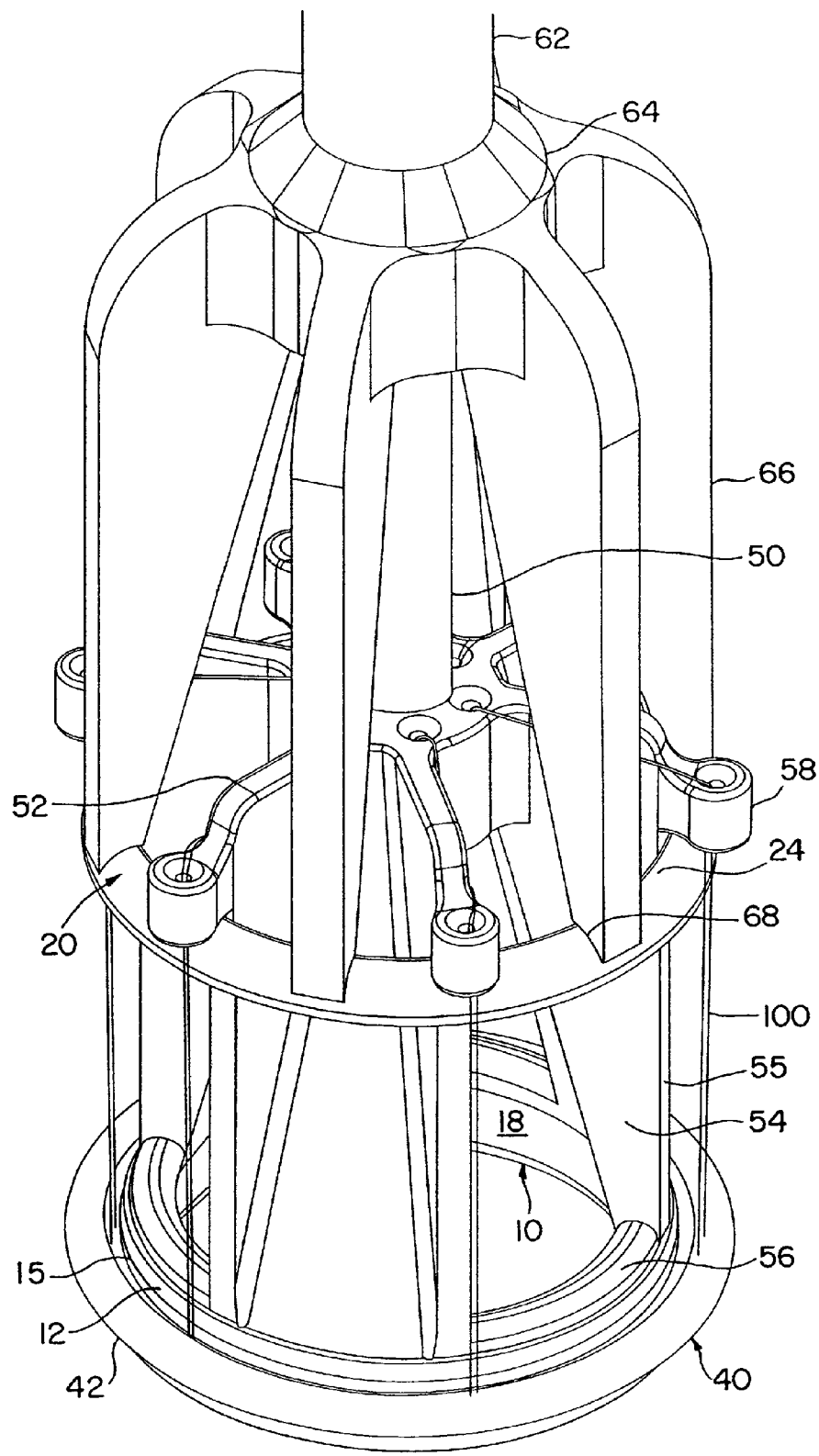
FIG. 9 depicts an expanded view of the insertion device of FIG. 8.

In FIG. 9, an expanded view of insertion device 2 of FIG. 8 is depicted. As described in FIG. 7, interior surface 22 of second cylinder 20 slidingly engages an exterior surface 55 of each of support 54. Sleeve end piece 64 has six securing brackets 66, which are adapted to engage second cylinder 20 with engaging surfaces 68. As noted above, securing brackets 66 are angularly offset and positioned to interfit with support brackets 54.

Figure 10:
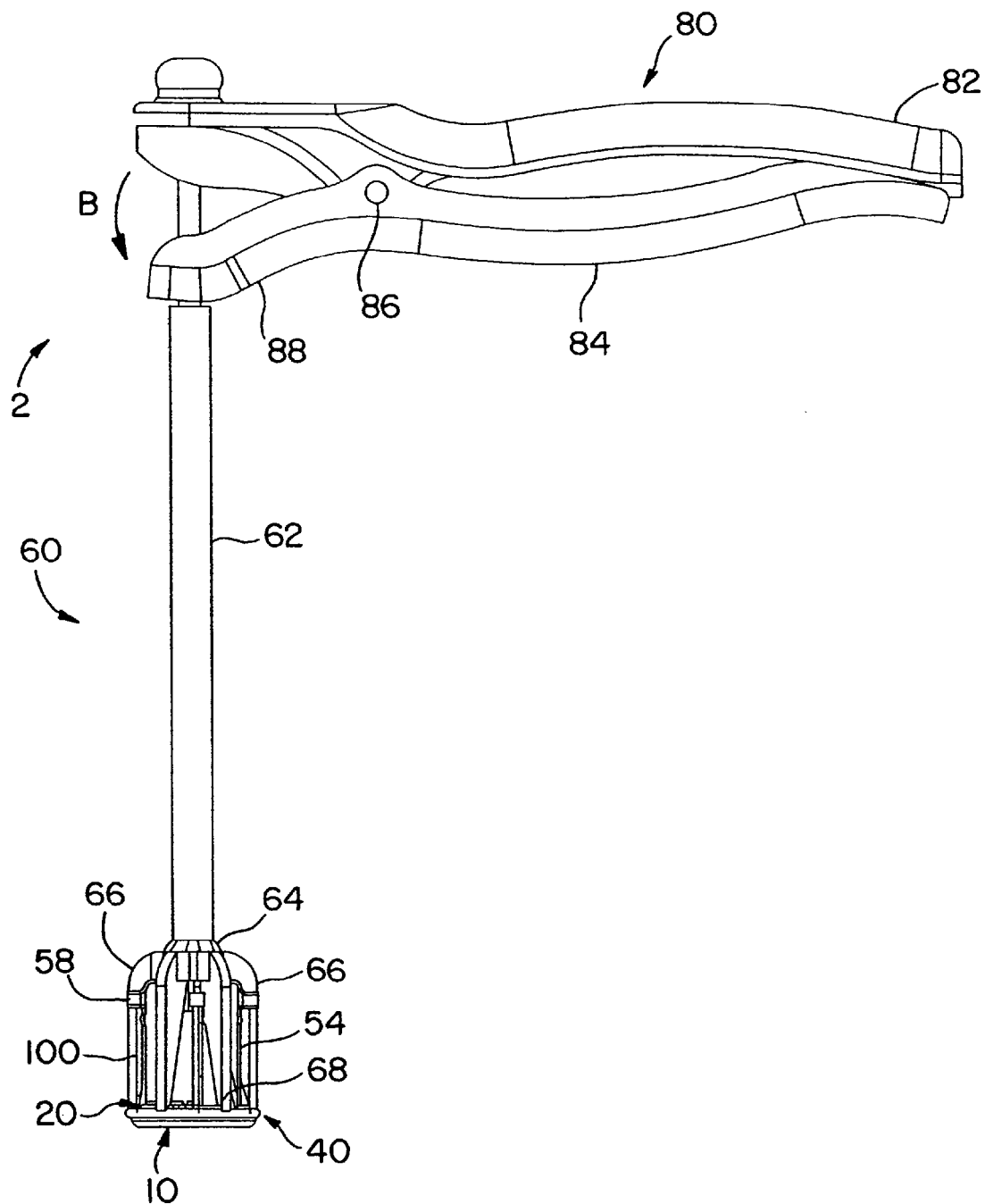
FIG. 10 depicts the insertion device of FIG. 8, with the urging member depressed, such that the second cylinder is snapped into engagement with the first cylinder.
Figure 11:
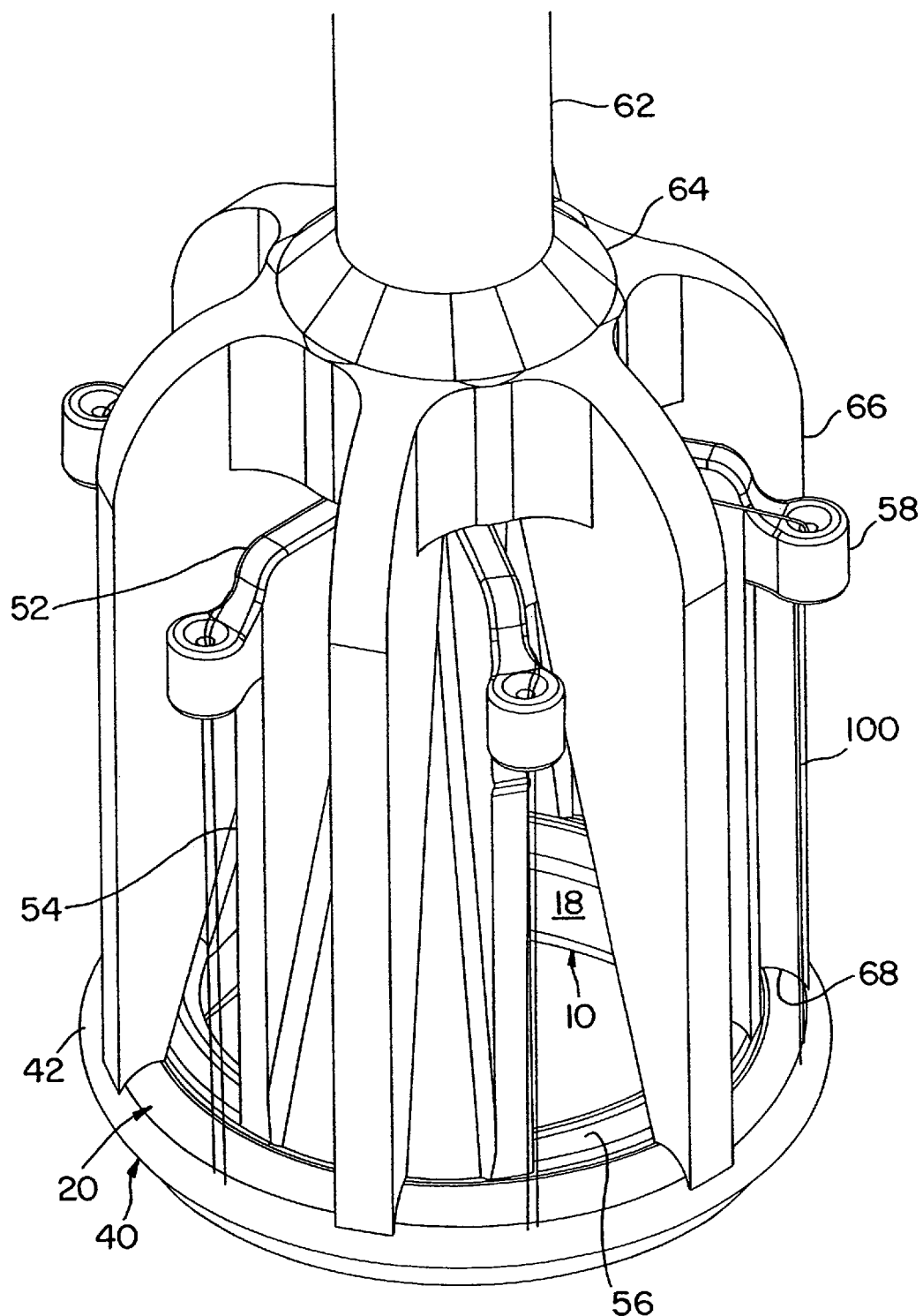
FIG. 11 depicts an expanded view of the insertion device of FIG. 10.

Referring to FIG. 10, insertion device 2 of FIG. 8 is depicted with urging member 80 depressed, such that second cylinder 20 is snapped into engagement with first cylinder 10. Specifically, grip 84 has been pivoted on pin 86 and thereby depressed against handle 82. Consequently, levered projection 88 is moved in the direction of Arrow B, and levered projection 88 contacts securing member 60 urging it toward rod end piece 52. As a result, securing brackets 66 interfit with support brackets 54, second cylinder 20 is urged into contact with first cylinder 10. As indicated in FIG. 11, an expanded view of insertion device 2 of FIG. 10 is depicted, showing second cylinder 20 urged into engagement with first cylinder 10.

In another embodiment, the invention is a method for automatically fixing sutures to secure a valve sleeve including an annular cuff and a replacement heart valve to an annulus formed in a patient's heart. The method comprises the steps of removing an existing heart valve, thereby forming an annulus in the patient's heart, and placing a first cylinder within the annulus. The first cylinder has a first end and a second end and an interior surface and an exterior surface and comprises first securing means formed on the exterior surface adjacent to the second end of the first cylinder. The first cylinder also includes a valve sleeve having an annular cuff, such that the annular cuff surrounds the exterior surface adjacent to the first end of the first cylinder. The method further comprises the steps of positioning the annular cuff of the valve sleeve in the annulus and securing the cuff to the annulus with a plurality of sutures, e.g., 18 to 24 sutures, and threading the plurality of sutures over the exterior surface of the first cylinder and over an interior surface of a second cylinder. As noted above, the second cylinder has second securing means corresponding to and adapted to fixedly engage the first securing means of the first cylinder. Pressure then is applied against the first cylinder, and tension is applied to the plurality of sutures to ensure a blood-tight seal between the cuff of the valve sleeve and the annulus. The plurality of sutures then are secured between the first cylinder and the second cylinder by engaging the first securing means of the first cylinder with the second securing means of the second cylinder. Finally, the plurality of sutures are trimmed at a length in a range of about 3 mm to about 5 trim, above the second cylinder, and preferably, the plurality of sutures are trimmed flush with the second cylinder.

In yet another embodiment, the invention is a method for automatically fixing sutures to secure a valve sleeve including an annular cuff and a replacement heart valve to an annulus formed in a patient's heart. The method comprises the steps of removing an existing heart valve, thereby forming an annulus in the patient's heart, and positioning the annular cuff of the valve sleeve in the annulus and securing the cuff to the annulus with a plurality of sutures. The method further comprises the steps of placing a first cylinder having a first end and a second end and an interior surface and an exterior surface and comprising first securing means formed on the exterior surface adjacent to the second end of the first cylinder, within the valve sleeve, such that the annular cuff surrounds the exterior surface adjacent to the first end of the first cylinder. The plurality of sutures are threaded over the exterior surface of the first cylinder and over an interior surface of a second cylinder. Pressure then is applied against the first cylinder, and tension is applied to the plurality of sutures to ensure a blood-tight seal between the cuff of the valve sleeve and the annulus. Finally, the method comprises the steps of securing the plurality of sutures between the first cylinder and the second cylinder by engaging the first securing means of the first cylinder with the second securing means of the second cylinder and trimming the sutures, as described above.

Although the invention has been described in the specification and drawings with respect to preferred embodiments, the invention is not limited to these preferred embodiments, but its true scope and spirit are defined be the following claims. The specification is intended merely to be exemplary of the invention, and persons skilled in the art will understand that modifications or alterations to the various features and components are possible without deviating from the scope and spirit of the invention.

We claim:

1. An apparatus for automatically fixing sutures used in the surgical replacement of a heart valve, comprising:
   a first cylinder having a first end and a second end and an interior surface and an exterior surface;
   first means for securing sutures formed on said exterior surface adjacent to said second end of said first cylinder; and
   a second cylinder having second means for securing sutures formed on an interior surface of said second cylinder, such that said second means corresponds to and fixedly engages said first means for securing sutures, wherein said first means and said second means secure sutures therebetween.

2. The apparatus of claim 1, wherein said first means is an annular lip and said second means is an annular groove.

3. The apparatus of claim 1, wherein said first means is an annular groove and said second means is an annular lip.

4. The apparatus of claim 1, further comprising a valve sleeve comprising an annular cuff and a plurality of securing struts surrounding said exterior surface adjacent to said first end of said first cylinder, said struts extending beyond said first end of said first cylinder.

5. The apparatus of claim 4, further comprising a replacement heart valve positioned within said valve sleeve and having a circumferential outer edge, wherein said circumferential outer edge is affixed to said valve sleeve.

6. The apparatus of claim 4, wherein said valve sleeve is manufactured from a surgical fabric.

7. The apparatus of claim 5, wherein said replacement heart valve comprises a heart valve harvested from a human donor.

8. The apparatus of claim 5, wherein said replacement heart valve comprises a heart valve harvested from a pig.

9. The apparatus of claim 5, wherein said replacement heart valve comprises a prosthetic heart valve.

10. An apparatus for automatically fixing sutures used in the surgical replacement of a heart valve, comprising:
    a first cylinder having a first end and a second end and an interior surface and an exterior surface;
    a valve sleeve comprising an annular cuff surrounding said exterior surface adjacent to said first end of said first cylinder,
    first means for securing sutures formed on said exterior surface adjacent to said second end of said first cylinder; and
    a second cylinder having second means for securing sutures formed on an interior surface of said second cylinder, such that said second means corresponds to and fixedly engages said first means for securing fixing sutures, wherein said first means and said second means secure sutures therebetween.

11. The apparatus of claim 10, wherein said cuff is manufactured from a surgical fabric.

12. The apparatus of claim 10, further comprising a prosthetic heart valve positioned within said first cylinder and affixed to said valve sleeve.

13. The apparatus of claim 10, wherein said first means is an annular lip and said second means is an annular groove.

14. The apparatus of claim 10, wherein said first means is an annular groove and said second means is an annular lip.

15. The apparatus of claim 10, further comprising a replacement heart valve positioned within said valve sleeve.

16. An apparatus for automatically fixing sutures used in the surgical replacement of a heart valve, comprising:
    a first cylinder having an interior surface, said first cylinder comprises an annular lip formed on said interior surface; and
    a second cylinder having an exterior surface, said second cylinder comprises an annular groove formed on said exterior surface,
    wherein said annular lip is configured to fixedly engage said annular groove to secure said interior surface of said first cylinder to said exterior surface of said second cylinder, and
    wherein said annular groove and said annular lip are configured to secure sutures therebetween.

* * * * *